(12) United States Patent
Mann et al.

(10) Patent No.: US 7,229,576 B2
(45) Date of Patent: Jun. 12, 2007

(54) SUBSTITUTED PHENANTHROPYRANS

(75) Inventors: Claudia Mann, Munich (DE); Manfred Melzig, Wessling (DE); Udo Weigand, Munich (DE)

(73) Assignee: Rodenstock GmbH, Munich (DE)

( * ) Notice: Subject to any disclaimer, the term of this patent is extended or adjusted under 35 U.S.C. 154(b) by 0 days.

(21) Appl. No.: 11/377,357

(22) Filed: Mar. 17, 2006

(65) Prior Publication Data

US 2006/0219990 A1     Oct. 5, 2006

Related U.S. Application Data

(63) Continuation of application No. PCT/EP2004/009369, filed on Aug. 20, 2004.

(30) Foreign Application Priority Data

Sep. 18, 2003  (DE)  ................................ 103 43 579

(51) Int. Cl.
  G02B 5/23    (2006.01)
  G02B 26/00   (2006.01)
  G02C 7/10    (2006.01)
  F21V 9/00    (2006.01)
  C07D 325/00  (2006.01)

(52) U.S. Cl. ...................... 252/586; 252/582; 359/238; 549/384

(58) Field of Classification Search ................. 252/586
See application file for complete search history.

(56) References Cited

U.S. PATENT DOCUMENTS

| | | |
|---|---|---|
| 3,567,605 A | 3/1971 | Becker |
| 4,272,190 A | 6/1981 | Shapiro |
| 4,800,270 A | 1/1989 | Blais |
| 4,826,977 A | 5/1989 | Heller et al. |
| 5,106,998 A | 4/1992 | Tanaka et al. |
| 5,187,364 A | 2/1993 | Blais |
| 5,238,981 A | 8/1993 | Knowles |
| 5,303,080 A | 4/1994 | O'Brien et al. |
| 5,514,817 A | 5/1996 | Knowles |
| 5,565,147 A | 10/1996 | Knowles et al. |
| 5,637,709 A | 6/1997 | Melzig |
| 5,674,432 A | 10/1997 | Knowles et al. |
| 5,748,315 A | 5/1998 | Kawai et al. |
| 5,796,222 A | 8/1998 | Grodevant |
| 5,869,658 A | 2/1999 | Lin et al. |
| 5,888,432 A | 3/1999 | Chan |
| 5,990,305 A | 11/1999 | Zinner et al. |
| 6,022,495 A | 2/2000 | Kumar |
| 6,037,583 A | 3/2000 | Moehler et al. |
| 6,154,270 A | 11/2000 | Ozawa |
| 6,210,608 B1 | 4/2001 | Chan et al. |
| 6,294,112 B1 | 9/2001 | Clarke et al. |
| 6,437,358 B1 | 8/2002 | Potucek et al. |
| 6,496,213 B1 | 12/2002 | Ueno |

FOREIGN PATENT DOCUMENTS

| | | |
|---|---|---|
| EP | 0 945 451 A1 | 9/1999 |
| EP | 1 038 870 A1 | 9/2000 |
| WO | WO 96/04576 A1 | 2/1996 |
| WO | WO 98/45281 A1 | 10/1998 |
| WO | WO 99/15518 A1 | 4/1999 |
| WO | WO 99/31082 A1 | 6/1999 |
| WO | WO 00/15628 A1 | 3/2000 |
| WO | WO 01/12619 A1 | 2/2001 |
| WO | WO 03/055872 A1 | 7/2003 |
| WO | WO 03/080595 A1 | 10/2003 |

OTHER PUBLICATIONS

International Search Report dated Jan. 21, 2005, including English Translation (Four (4) pages). PCT/EP2004/009369.

*Primary Examiner*—Randy Gulakowski
*Assistant Examiner*—Timothy J. Kugel
(74) *Attorney, Agent, or Firm*—Crowell & Moring LLP.

(57) ABSTRACT

The present invention relates to specific photochromic phenanthropyrans as well as to their use in synthetic resin materials of all types, especially for ophthalmic purposes. In particular, the present invention relates to photochromic compounds derived from 2H-phenanthro[2,1-b]pyrans and 3H-phenanthro[3,4-b]pyrans, which in the open form have especially long wavelength absorption maxima, but in the unexcited state are still colorless.

9 Claims, 1 Drawing Sheet

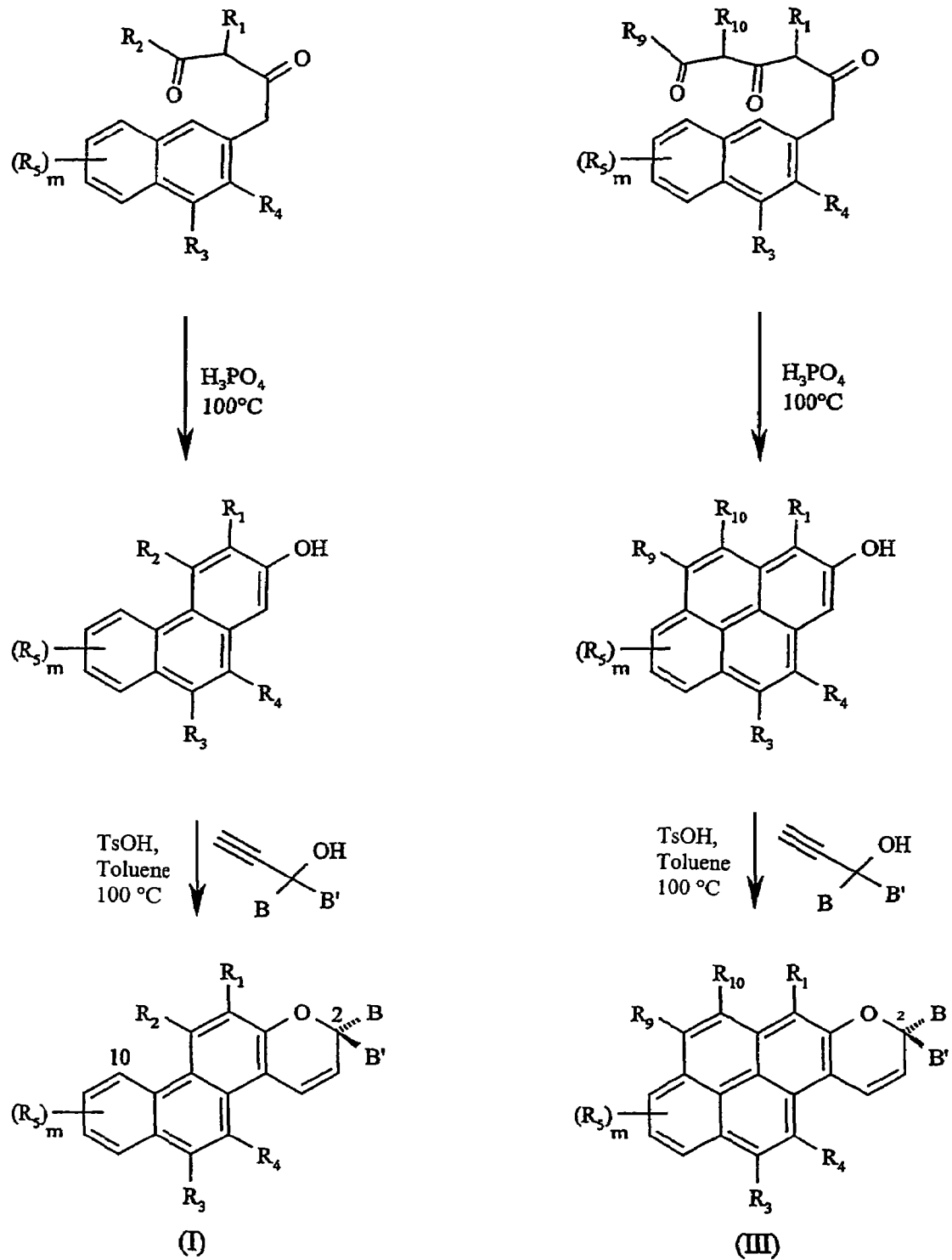

SUBSTITUTED PHENANTHROPYRANS

CROSS REFERENCE TO RELATED APPLICATIONS

This application is a continuation of international patent application no. PCT/EP2004/009369, filed Aug. 20, 2004, designating the United States of America, and published in German on Apr. 21, 2005 as WO 2005/035529, the entire disclosure of which is incorporated herein by reference. Priority is claimed based on Federal Republic of Germany patent application no. DE 103 43 579.4, filed Sep. 18, 2003.

BACKGROUND OF THE INVENTION

The present invention relates to specific photochromic phenanthropyrans, as well as to their use in synthetic resin materials of all types, especially for ophthalmic purposes. In particular, the present invention relates to photochromic compounds, which are derived from 2H-phenanthro[2,1-b]pyrans and 3H-phenanthro[3,4-b]pyrans, which, in the open form, have particularly long-wave absorption maxima, but are still colorless in the unexcited state.

Different classes of dyes are known, which, when irradiated with light of particular wavelengths, especially sunlight, change their color reversibly. This comes about because of the fact that, due to the supply of energy in the form of light, these dye molecules transition into an excited, colored state, which they leave once again when the supply of energy is interrupted, as a result of which they return to their colorless or hardly colored normal state. These photochromic dyes include, for example, the naphthopyrans, which have already been described in the state of the art with different substituents.

Pyrans, especially naphthopyrans and larger ring systems derived from naphthopyrans, are photochromic compounds, which have been the subject of intensive investigations up to the present time. Although the first patents were applied for as early as 1966 (U.S. Pat. No. 3,567,605), compounds, which appeared to be suitable for use in lenses for eyeglasses, were developed only in the 1990s.

The dyes, known from the prior art, frequently have inadequate long-wave absorption in the excited as well as in the unexcited state. This leads to problems even when such dyes are combined with other photochromic dyes. Furthermore, such dyes frequently also exhibit an excessively high temperature sensitivity with respect to the darkening and, at the same time, the lightening or fade is too slow. Moreover, the durability of the dyes available in the prior art frequently is insufficient. Consequently, the durability of such lenses for sunglasses is inadequate. This becomes noticeable due the rapidly decreasing performance and/or the strong yellowing which occurs.

3H-Naphthopyrans, derived from 2-naphthols, and their higher analog derivatives derived by annellation constitute a group of photochromic dyes, the longest wavelength absorption maximum of the excited form of which lies predominantly in the spectral range from 420 nm to 500 nm and accordingly cause a yellow, orange or red-orange color sensation (see U.S. Pat. Nos. 5,869,658 and 6,022,495). However, high-performance, violet to blue photochromic dyes are required for neutral, darkening phototropic glasses. Violet to blue photochromic dyes which are currently available in the art, usually originate from the class of spiroxazine dyes, fulgide dyes or 2H-naphtho[1,2-b]pyrans. Usually, however, spiroxazine dyes are disadvantageous with respect to their high-temperature performance, and fulgide dyes and 2H-naphtho[1,2-b]pyrans have properties which are not completely satisfactory for use in lenses for sunglasses, the former because of the durability and the latter because of the lightening rate.

The introduction of electron-displacing substituents on the aryl groups in the ortho position to the pyran oxygen, as described, for example, in WO 98/45281, WO 01/12619 and EP 0 945 451 A1 leads to red or red violet darkening 3H-naphtho[2,1-b]pyrans. WO 01/12619 discloses compounds in which one geminal aryl group has a para-aminosubstituted group and the other aryl group has an alkoxy group or a thioalkoxy group, substituted in the meta or para position, this substitution pattern having a positive effect on the lightening rate. WO 98/45281 describes red hyperchromic compounds which additionally contain an amine function predominantly in the 6-position of the 3H-naphtho[2,1-b]pyran unit. Compounds, with amino groups which do not have pronounced basic properties are described in EP 0 945 451 A1. In the excited state, these compounds show a pink to violet color and have an attractive durability. 3H-Naphtho[2,1-b]pyrans with an aryl substituent in the 6-position are furthermore described in WO 99/31082. The effect of the aryl substitution in the 6-position on the longest wavelength absorption maximum of the unexcited as well as the excited form is, however, very slight in these compounds.

Appropriate substitution in the 8-position of the 3H-naphtho[2,1-b]pyran unit brings about a bathochromic shift in the longest wavelength absorption maximum, especially due to the introduction of alkoxy groups, as described in U.S. Pat. No. 5,238,981. In addition, compounds with dialkylamino groups in the 8-position are also disclosed. The use of nitrogen heterocyclic groups as substituents in the 8-position of the 3H-naphtho[2,1-b]pyran unit is mentioned in U.S. Pat. No. 5,990,305, as a result of which, in contrast to open-chain amino groups, an improved durability is obtained. This is also achieved with substituents which contain so-called HALS (hindered amine light stabilizer) structural units. Finally, violet to blue 3H-naphthol[2,1-b]pyrans, which have substituents containing amino groups in the 3-position as well as in the 8-position, are described in WO 03/055872, and blue 3H-naphthol[2,1-b]pyrans which contain a substituent in the 6-position in addition to the above substituents in the 3 and 8-positions are described in WO 03/080595.

Larger aromatic ring systems, which contain a naphthopyran unit, are described, for example, in U.S. Pat. Nos. 5,106,998, 5,888,432, 4,826,977 and 5,637,709. However, the compounds are not substituted with two aryl groups in the 3-position and instead have at least one saturated polycyclic substituent and thus lead to yellow to red photochromic compounds in the excited form.

Furthermore, U.S. Pat. Nos. 5,565,147, 5,674,432 and 6,294,112 (WO 98/45281) disclose photochromic 3H-naphtho[2,1-b]pyrans which have an annellated heterocyclic unit at the different sides of the naphthalene unit. Accordingly, red hyperchromic 3H-naphtho[2,1-b]pyrans, which may be annellated heterocyclically, are described in U.S. Pat. No. 6,294,112 (WO 98/45281). EP 1 038 870 A1 describes 3H-naphtho[2,1-b]pyrans which have an optionally substituted amido group in the 5-position and the naphthopyran unit of which may be expanded by a heterocyclic or aromatic ring.

Substituted phenanthropyrans are described in U.S. Pat. Nos. 5,514,817 and 6,210,608. These are derived, however, from 2H-naphtho[1,2-b]pyrans.

SUMMARY OF THE INVENTION

Accordingly, it is an object of the present invention to provide improved photochromic dyes.

Another object of the invention is to provide photochromic compounds which are colorless in the unexcited form and differ from comparable prior art compounds by an especially advantageous combination of long wavelength absorption and high darkening performance in the excited state.

A further object of the invention is to provide photochromic compounds which simultaneously exhibit both good kinetic and durability properties, i.e., which have both a rapid lightening rate and perform well in the durability test.

These and other objects are achieved in accordance with the present invention as described and claimed hereinafter.

In particular, 2H-phenanthro[2,1-b]pyrans corresponding to Formula (I) and 3H-phenanthro[3,4-b]pyrans corresponding to Formula (II) are provided

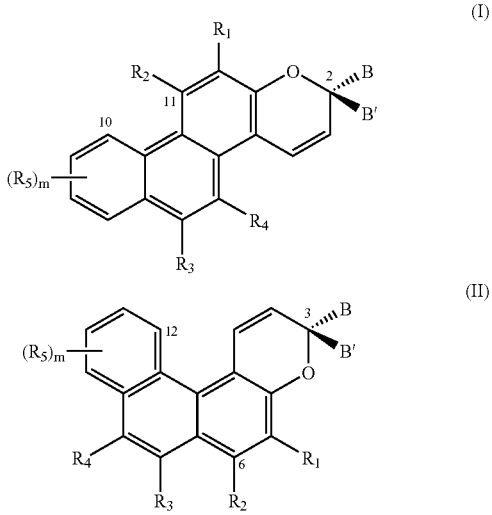

in which m is a whole number from 0 to 3, the $R_1$, $R_2$, $R_3$, $R_4$ and $R_5$ groups independently of one another, represent hydrogen or a substituent, selected from the group α consisting of fluorine, chlorine, bromine, hydroxy, silyloxy, a linear or branched ($C_1$–$C_6$) alkyl group, a ($C_3$–$C_7$) cycloalkyl group, a linear or branched ($C_1$–$C_6$) alkoxy group, phenyl, phenoxy, benzyl, benzyloxy, naphthyl, naphthoxy, phenanthryl or pyridyl, which may be substituted in each case with one, two or three substituents selected independently from one another from the group β consisting of linear or branched ($C_1$–$C_6$) alkyl groupss, ($C_3$–$C_7$) cycloalkyl groups, linear or branched ($C_1$–$C_6$) alkoxy groups, hydroxy, t-butyldiphenylsilyloxy, amino, di($C_1$–$C_6$)alkylamino, nitro, cyano, benzyl, 4-methoxybenzyl, 4-nitrobenzyl, phenyl, 4-methoxyphenyl, 4-dimethylaminophenyl, pyridyl and pyrimidinyl, or an $NR_6R_7$ group, wherein the R6 and $R_7$ groups, independently of one another are selected from hydrogen, linear or branched ($C_1$–$C_6$) alkyl groups, ($C_3$–$C_7$) cycloalklyl groups, phenyl or benzyl, wherein the latter two optionally have one or more substituents from the group β, or the $R_6$ and $R_7$ groups together with the nitrogen atom form an azaadamantyl group or a 3- to 10-membered nitrogen heterocyclic group, which is unsubstituted or may be substituted with a linear or branched ($C_1$–$C_6$) alkyl group, wherein the nitrogen heterocyclic group optionally contains one or more heteroatoms selected from the group consisting of O, S and $NR^8$, wherein the $R^8$ group is selected from hydrogen or the group β, and wherein the nitrogen heterocyclic group optionally may be annellated with one or two benzene rings; or two adjacent $R_5$ groups together form an unsubstituted, monosubstituted or disubstituted annellated benzene ring, the substituents of which, independently of one another, are selected from the group α or from the above-defined $NR_6R_7$ group; or the $R_3$ group together with the $R^4$ group forms an unsubstituted, monosubstituted or disubstituted, annellated benzene ring with the formation of a triphenylenepyran, the substituents of which are independently selected from the group α or an $NR_6R_7$ group as defined above;

the $R_2$ group is selected from hydrogen or a substituent of the group α, an above-defined $NR_6R_7$ group or quinolinyl, isoquinolinyl, thienyl, benzothienyl, dibenzothienyl, furanyl, benzofuranyl, dibenzofuranyl, carbazolyl, phenothiazinyl, phenoxazinyl, oxazolyl, benzoxazolyl, oxadiazolyl, thiazolyl, benzothiazolyl, thiadiazolyl, imidazolyl, pyrazolyl, triazolyl, tetrazolyl, pyrimidinyl, pyrazinyl, acetyl, benzoyl, cyano, formyl, iminomethyl, 1-iminoaminomethyl, N-hydroxyiminomethyl, methyleneamino, cyanamino, cyanomethyl, dicyanomethyl, carboxy, carboxymethyl, ($C_1$–$C_6$) acyloxy, ($C_1$–$C_6$) alkoxycarbonyl, ($C_1$–$C_6$) alkoxycarbonyl methyl, phenoxycarbonyl, benzyloxycarbonyl, nitro, diazophenyl, aminocarbonyl, ethenyl, 4-ethenylphenyl, ethinyl or 4-ethinylphenyl or, with formation of a catatonic structure from N-($C_1$–$C_6$)-alkylpyridinio, 1-pyridinio, N-($C_1$–$C_6$)-alkylquinlinio, 1-quinolinio, N-($C_1$–$C_6$)-alkylisoquinolinio, 2-isoquinolinio, iminomethyl or 1-iminioaminomethyl, whereby the corresponding counterion is selected from chloride, bromide, sulfate, hydrogen sulfate, tetrafluoroborate, hexafluorophosphate, mesylate, tosylate or triflate, the above substituents, as far as possible, having one, two, three or four substituents from the group β; or the $R_1$ and $R_2$ groups in Formula (I) or the $R_1$ and $R_2$ or $R_2$ and $R_3$ groups in Formula (II) form an aromatic or heteroaromatic ring, annellated to the phenanthrene unit and selected from a benzene ring, a pyridine ring, an indole ring, a benzofuryl ring, a benzothienyl ring, a thienyl ring, a furyl ring or a pyrimidinyl ring, which, in each case, may be substituted with one or more substituents from the group a, and, in the case of an indole ring, a benzofuryl ring or a benzothienyl ring, the annellation to the phenanthrene framework taking place through the 5-membered heterocyclic group; or the $R_2$ group together with an $R_5$ group in the 10-position of the phenanthrene system of Formula (I) forms an annellated benzene ring with the formation of a pyrenopyran of Formula (III) below

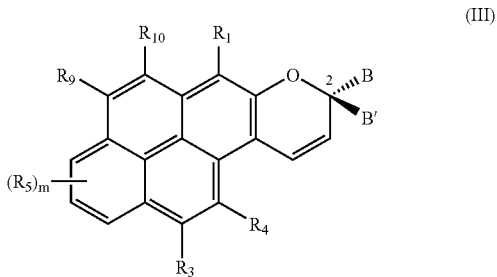

or an annellated pyrido ring, wherein the nitrogen atom replaces the carbon atom connected with $R_9$ or $R_{10}$, the annellated benzene ring optionally being substituted with the $R_9$ and $R_{10}$ groups and the annellated pyrido ring with an $R_9$ group, wherein $R_9$ or $R_9$ and $R_{10}$, independently of one another, are selected from the group α, or wherein the $R_9$ and $R_{10}$ groups in Formula (III) once again together form an annellated, aromatic or heteroaromatic ring, selected from a benzene ring, a pyridine ring, an indole ring, a benzofuryl ring, a benzothienyl ring, a thienyl ring, a furyl ring or a pyrimidinyl ring, which in each case may be substituted with one or more substituents from the group α, and in the case of an indole ring, a benzofurinyl ring or a benzothienyl ring, the annellation taking place through a 5-membered heterocyclic ring; and B and B' independently of one another are selected from unsubstituted, monosubstituted or disubstituted phenyl, ethinyl, ethenyl, naphthyl, furanyl, benzofuranyl, thienyl, benzothienyl or julolidinyl, the substituents being selected from the group α, an $NR_6R_7$ group as defined above, as well as ethenyl, 4-ethenylphenyl, ethinyl or 4-ethinylphenyl, wherein the substituents of the group α, as well as the above substituents, as far as possible, once again, independently of one another, may have two or three substituents from the group β, or wherein two directly adjacent substituents represent a Y—$(CH_2)_q$—Z group, in which q=1, 2 or 3 and Y and Z, independently of one another, may be oxygen, sulfur, $NCH_3$, NPh, $CH_2$, $C(CH_3)_2$ or $C(C_6H_5)_2$, or B and B' together represent an unsubstituted, monosubstituted or disubstituted 9-spirofluorene, wherein the fluorene substituents are selected from the group β, or B and B' together represent a saturated hydrocarbon, which is $C_3$–$C_{12}$ spiromonocyclic, $C_7$–$C_{12}$ spirobicyclic or $C_7$–$C_{12}$ spirotricyclic.

The enlargement of the basic aromatic system by benzoannellation at the g side or the i side of 3H-naphtho[2,1-b]pyrans leads to 2H-phenanthro[2,1-b]pyrans or 3H-phenanthro[3,4-b]pyrans, which are still colorless in the unexcited form and have a high extinction. The photochromic properties of the dyes, especially their output, can be increased even further by the simultaneous introduction of appropriate substituents, which, in the excited form, lead to absorption by the compounds at longer wavelengths, and/or the simultaneous introduction of appropriate substituents in the 11-position of the compounds of Formula (I) or in the 6-position of the compounds of Formula (II). In comparison to comparable compounds of the prior art, the compounds of the invention absorb at longer wavelengths while, at the same time, their darkening performance is equally good. Moreover, the photochromic 2H-phenanthro[2,1-b]pyrans and 3H-phenanthro[3,4-b]pyrans according to the invention exhibit good durability and rapid lightening rates. At the same time, their darkening performance is exceptional.

m is 0 to 3 since, for steric reasons, there usually is no substituent in the peri position, that is, in the 10-position, with the exception of the present case, in which $R_5$ together with $R_2$ forms an annellated benzo ring or pyrido ring.

BRIEF DESCRIPTION OF THE DRAWING

The accompanying drawing is a schematic representation of a reaction scheme for synthesizing the compounds of the invention of Formula I and Formula III.

DETAILED DESCRIPTION OF PREFERRED EMBODIMENTS

In one embodiment of the present invention, the groups $R_1$, $R_3$, R4 and $R_5$, independently of one another, are selected from hydrogen, a substituent from the group α or an —$NR_6R_7$ group as defined above.

In a further embodiment of the present invention, at least one of the B and B' groups is a phenyl group substituted in the para position with an —$NR_6R_7$ group as defined above. In this connection, the $R_6$ and $R_7$ groups, together with the nitrogen atom of this —$NR_6R_7$ group, may also form an azaadamantyl group. Alternatively, they may also form a 3-membered to 10-membered nitrogen heterocyclic ring as already defined above, especially a morpholine group, a thiomorpholine group, a piperidine group, an azacycloheptane group, an azacyclooctane group, a 1,4-diaza-1-methylcycloheptane group, a piperazine group, an —N-(N—-($C_1$–$C_6$-alkyl)piperazine group or a pyrrolidone group, or the phenyl group substituted in the para position with an —$NR_6R_7$ group, represents, as a whole, an N-methyl-1,2,3,4-tetrahydroquinoliniyl group, so that the following structure unit is present.

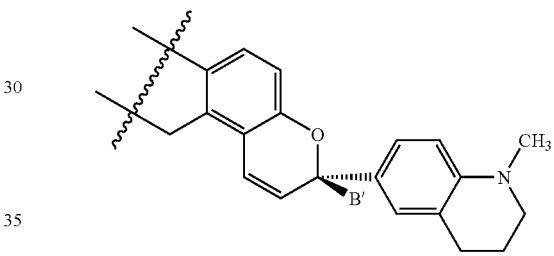

In a different embodiment, at least one of the B and B' groups preferably is a 4-dimethylaminophenyl group.

If one of the B and B' groups represents a julodinyl group, linked to the pyran ring at the 3-position, the following structural unit results:

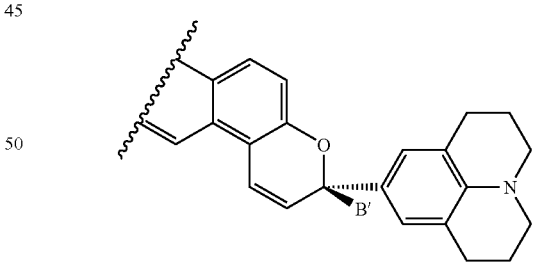

In a further, preferred embodiment of the present invention, the $R_2$ group in Formulas (I) and (II) is selected from ($C_1$–$C_6$) alkyl, phenyl, 4-methoxyphenyl, 4-dimethylaminophenyl, ethenyl, ethinyl, 2-(($C_1$–$C_6$)-alkyl)ethenyl, 2-(($C_1$–$C_6$)-alkyl)ethinyl, 2-phenylethenyl or 2-phenylethinyl.

In a different preferred embodiment of the present invention, the $R_9$ group in Formula (III) is selected from ($C_1$–$C_6$) alkyl, phenyl, 4-methoxyphenyl, 4-dimethylaminophenyl, ethenyl, ethinyl, 2-(($C_1$–$C_6$)-alkyl)ethenyl, 2-(($C_1$–$C_6$)-alkyl)-ethinyl, 2-phenylethenyl or 2-phenylethinyl.

Particularly preferred photochromic 2H-phenanthro[2,1-b]pyrans of Formula (I) according to the present invention have the following combination of substituents:

$R_1$, $R_3$, $R_4$ and $R_5$ each represent hydrogen,
$R_2$ represents ($C_1$–$C_6$)-alkyl, phenyl, 4-methoxyphenyl, 4-dimethylaminophenyl, ethenyl, ethinyl, 2-(($C_1$–$C_6$)-alkyl)ethenyl, 2-(($C_1$–$C_6$)-alkyl)ethinyl, 2-phenylethenyl or 2-phenylethinyl,
B' represents phenyl,
B is selected from 4-dimethylaminophenyl or 4—(N-azacycloheptyl) phenyl.

Particularly preferred photochromic pyrenopyrans of Formula (III) according to the present invention have the following combination of substituents:

$R_1$, $R_3$, $R_4$ and $R_5$ each represent hydrogen,
$R_2$ represents ($C_1$–$C_6$)-alkyl, phenyl, 4-methoxyphenyl, 4-dimethylamino-phenyl, ethenyl, ethinyl, 2-(($C_1$–$C_6$)-alkyl)ethenyl, 2-(($C_1$–$C_6$)-alkyl)ethinyl, 2-phenylethenyl or 2-phenylethinyl,
B' represents phenyl,
B is selected from 4-dimethylaminophenyl or 4-(N-azacycloheptyl) phenyl.

The longest wavelength absorption maxima of the open (colored) form of representative examples of the compounds of Formula (I) are given in the following Table:

| No. | $R_2$ | B | B' | $R_1$, $R_3$, $R_4$, $R_5$ | Longest wavelength absorption maximum of the open (colored) form |
|---|---|---|---|---|---|
| 1 | $CH_3$ | 4-dimethyl-aminophenyl | Ph | H | 560 nm |
| 2 | 4-dimethyl-aminophenyl | 4-(N-aza-cycloheptyl)-phenyl | Ph | H | 580 nm |
| 3 | 2-(t-butyl)-ethenyl | 4-(N-aza-cycloheptyl)-phenyl | Ph | H | 585 nm |

$\lambda_{max}$: longest wavelength absorption maximum of the open (colored) form [measured in methacrylate polymer]

The longest wavelength absorption maxima of the open (colored) form of representative example compounds of Formula (III) are given in the following Table:

| No. | $R_9$ | B | B' | $R_1$, $R_3$, $R_4$, $R_5$, $R_{10}$ | Longest wavelength absorption maximum of the open (colored) form |
|---|---|---|---|---|---|
| 1 | $CH_3$ | 4-dimethylamino-phenyl | Ph | H | 595 nm |
| 2 | Ph | 4-(N-aza-cyclo-heptyl)phenyl | Ph | H | 610 nm |

$\lambda_{max}$: longest wavelength absorption maximum of the open (colored) form [measured in methacrylate polymer]

The compounds according to the invention may be used in synthetic resin materials or synthetic resin objects of any kind or shape for a variety of purposes for which photochromic activity is of importance. Moreover, a dye of the present invention or a mixture of such dyes may be used. For example, the photochromic 2H-phenanthro[2,1-b]pyrans and 3H-phenanthro[3,4-b]pyrans according to the invention may be used in lenses, especially in ophthalmic lenses, glasses for spectacles of all types, such as ski goggles, sunglasses, motorbike spectacles, visors of safety helmets and the like. Furthermore, the photochromic dyes according to the invention may also be used, for example, as protection against the sun in vehicles and living rooms in the form of windows, protective shutters, coverings, roofs or the like.

In order to produce such photochromic objects, the photochromic 2H-phenanthro[2,1-b]pyrans and 3H-phenanthro[3,4-b]pyrans of the invention may be applied by different methods, described in the art, as in WO 99/15518, onto a polymer material, such as an organic synthetic resin material, or embedded therein.

A distinction is made between so-called bulk dyeing methods and surface dyeing methods. A bulk dyeing method comprises, for example, the dissolving or dispersing of the photochromic compound or compounds of the present invention in a synthetic resin material, for example, by addition of the photochromic compound or compounds to a monomeric material, before polymerization takes place. A further possibility for producing a photochromic object is to permeate the synthetic resin material or materials with the photochromic compound or compounds by immersing the synthetic resin material in a hot solution of the photochromic dye or dyes of the present invention or, for example, also by a heat transfer process. The photochromic compound or compounds may also be used, for example, in the form of a separate layer between adjoining layers of the synthetic resin material, for example, as part of a polymeric film. Furthermore, it is also possible to apply the photochromic compound or compounds as part of a coating on the surface of the synthetic resin material. In this connection, the expression "permeate" denotes the migration of the photochromic compound of compounds into the synthetic resin material, for example, by the solvent-supported transfer of the photochromic compound or compounds into a polymer matrix, by vapor-phase transfer or by other such surface diffusion processes. Advantageously, photochromic objects such as eyeglass lenses can be produced not only by the usual bulk dyeing but, in a similar manner, also by surface diffusion, whereby in the latter variant, a surprisingly lower tendency to migrate can be achieved. This is of advantage especially during subsequent finishing steps, since, for example, during an anti-reflection coating, layer detachments and similar defects can be reduced drastically as a result of the lesser back-diffusion under a vacuum.

Overall, on the basis of the photochromic 2H-phenanthro[2,1-b]pyran dyes and 3H-phenanthro[3,4-b]pyran dyes according to the invention, any dyeings, that is, dyes, which are compatible from a chemical or color point of view, may be applied on or embedded in the synthetic resin material in order to satisfy the aesthetic points of view as well as medical or fashion aspects. The specific dye or dyes selected may accordingly vary, depending on the intended effects as well as the requirements.

The photochromic 2H-phenanthro[2,1-b]pyran dyes according to the invention of the general Formula (I) or those derivatives of Formula (III) can be synthesized according to the reaction outline shown in FIG. 1.

The key steps of the syntheses of the compounds according to the invention are cyclizations starting out from the corresponding 1,3-diketone derivatives or 1,3,5-triketone derivatives, that is, from 4-(2-naphthyl)-1,3-butadione derivatives or 6-(2-naphthyl)-1,3,5-hexatrione derivatives by means of phosphoric acid at about 100° C. Subsequently, the resulting hydroxyphenanthrene or hydroxypyrene derivatives are reacted with suitably substituted 2-propine-1-ol derivatives to form the compounds according to the invention.

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations within the scope of the appended claims and equivalents thereof.

What is claimed is:

1. A photochromic phenanthropyran compound corresponding to Formula (I) or Formula (II):

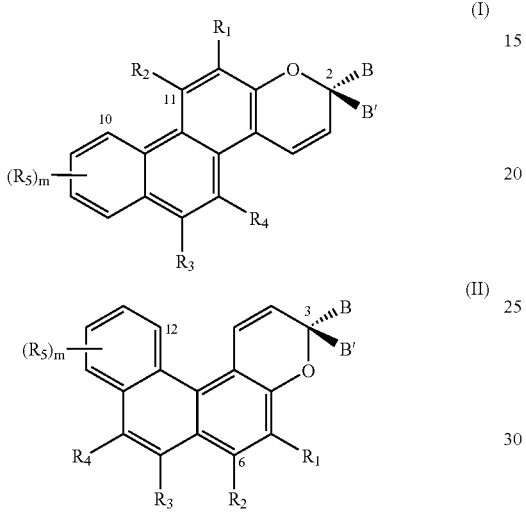

wherein m is a whole number from 0 to 3;

$R_1$, $R_3$, $R_4$ and $R_5$ are each independently hydrogen or a substituent selected from the group α consisting of fluorine, chlorine, bromine, hydroxy, silyloxy, a linear or branched ($C_1$–$C_6$) alkyl group, a ($C_3$–$C_7$) cycloalkyl group, a linear or branched ($C_1$–$C_6$) alkoxy group, phenyl, phenoxy, benzyl, benzyloxy, naphthyl, naphthoxy, phenanthryl and pyridyl, each of which may be substituted with one, two or three substituents independently selected from the group β consisting of a linear or branched ($C_1$–$C_6$) alkyl group, a ($C_3$–$C_7$) cycloalkyl group, a linear or branched ($C_1$–$C_6$) alkoxy group, hydroxy, t-butyldiphenylsilyloxy, amino, di($C_1$–$C_6$) alkylamino, nitro, cyano, benzyl, 4-methoxybenzyl, 4-nitrobenzyl, phenyl, 4-methoxyphenyl, 4-dimethylaminophenyl, pyridyl and pyrimidinyl, or an $NR_6R_7$ group wherein $R_6$ and $R_7$ are independently selected from the group consisting of hydrogen, a linear or branched ($C_1$–$C_6$) alkyl group, a ($C_3$–$C_7$) cycloalklyl group, phenyl and benzyl, wherein phenyl and benzyl optionally may be substituted with at least one substituent selected from the group β, or wherein $R_6$ and $R_7$ together with the nitrogen atom to which they are attached form an azaadamantyl group or a 3- to 10-membered nitrogen heterocyclic group optionally substituted with a linear or branched ($C_1$–$C_6$) alkyl group, and wherein the nitrogen heterocyclic group optionally contains one or more heteroatoms selected from the group consisting of O, S and $NR^8$, wherein $R_8$ is selected from hydrogen or the group β, and wherein the nitrogen heterocyclic group optionally is annellated with one or two benzene rings; or two adjacent $R_5$ groups together form an unsubstituted, monosubstituted or disubstituted annellated benzene ring, the substituents of which are independently selected from the group α or an $NR_6R_7$ group as defined above; or $R_3$ and $R^4$ together form an unsubstituted, monosubstituted or disubstituted, annellated benzene ring with the formation of a triphenylenepyran, the substituents of which are independently selected from the group α or an $NR_6R_7$ group as defined above;

$R_2$ is hydrogen or a substituent of the group α, or an $NR_6R_7$ group as defined above, or quinolinyl, isoquinolinyl, thienyl, benzothienyl, dibenzothienyl, furanyl, benzofuranyl, dibenzofuranyl, carbazolyl, phenothiazinyl, phenoxazinyl, oxazolyl, benzoxazolyl, oxadiazolyl, thiazolyl, benzothiazolyl, thiadiazolyl, imidazolyl, pyrazolyl, triazolyl, tetrazolyl, pyrimidinyl, pyrazinyl, acetyl, benzoyl, cyano, formyl, iminomethyl, 1-iminoaminomethyl, N-hydroxyiminomethyl, methyleneamino, cyanamino, cyanomethyl, dicyanomethyl, carboxy, carboxymethyl, ($C_1$–$C_6$)-acyloxy, ($C_1$–$C_6$)-alkoxycarbonyl, ($C_1$–$C_6$)-alkoxycarbonylmethyl, phenoxycarbonyl, benzyloxycarbonyl, nitro, diazophenyl, aminocarbonyl, ethenyl, 4-ethenylphenyl, ethinyl or 4-ethinylphenyl, or a cationic structure formed from a N-($C_1$–$C_6$)-alkylpyridinio, 1-pyridinio, N-($C_1$–$C_6$)-alkylquinolinio, 1-quinolinio, N-($C_1$–$C_6$)-alkylisoquinolinio, 2-isoquinolinio, iminomethyl or 1-iminioaminomethyl group, with an associated anion selected from the group consisting of chloride, bromide, sulfate, hydrogen sulfate, tetrafluoroborate, hexafluorophosphate, mesylate, tosylate and triflate; the foregoing substituents, as far as possible, each having one, two, three or four substituents selected from the group β; or $R_1$ and $R_2$ in Formula (I), or $R_1$ and $R_2$, or $R_2$ and $R_3$ in Formula (II) form an aromatic or heteroaromatic ring annellated to the phenanthrene unit and selected from a benzene ring, a pyridine ring, an indole ring, a benzofuryl ring, a benzothienyl ring, a thienyl ring, a furyl ring and a pyrimidinyl ring, each of which optionally may be substituted with one or more substituents selected from the group α, and, in the case of an indole ring, a benzofuryl ring or a benzothienyl ring, the annellation to the phenanthrene framework takes place through the 5-membered heterocyclic ring; or $R_2$ together with an $R_5$ group in the 10-position of the phenanthrene system of Formula (I) forms an annellated benzene ring to yield a pyrenopyran corresponding to Formula (III):

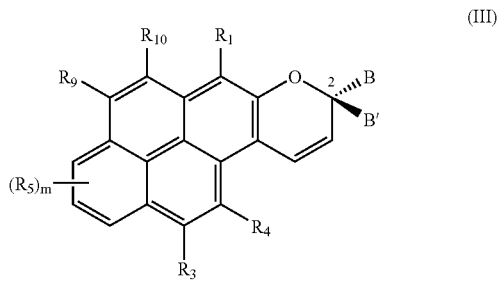

or an annellated pyrido ring, wherein the nitrogen atom replaces the carbon atom bonded to $R_9$ or $R_{10}$, wherein the annellated benzene ring optionally may be substituted with the groups $R_9$ and $R_{10}$ and the annellated pyrido ring optionally may be substituted with an $R_9$ group, wherein $R_9$ or $R_9$ and $R_{10}$ are independently selected from the group α, or wherein $R_9$ and $R_{10}$ in Formula (III) together form an annellated, aromatic or heteroaromatic ring selected from the group consisting of a benzene ring, a pyridine ring, an indole ring, a benzofuryl ring, a benzothienyl ring, a thienyl ring, a furyl ring and a pyrimidinyl ring, each of which optionally may be substituted with one or more substituents selected from the group α, and in the case of an indole ring, a benzofurinyl ring or a benzothienyl ring, the annellation takes place through the 5-membered heterocyclic ring; and

- B and B' are independently selected from unsubstituted, monosubstituted or disubstituted phenyl, ethinyl, ethenyl, naphthyl, furanyl, benzofuranyl, thienyl, benzothienyl and julolidinyl, wherein the substituents are selected from the group consisting of the group α, an $NR_6R_7$ group as defined above, ethenyl, 4-ethenylphenyl, ethinyl and 4-ethinylphenyl, wherein the foregoing substituents, as far as possible, each independently optionally may be substituted with two or three substituents selected from the group β, or wherein two directly adjacent substituents represent a $Y—(CH_2)_q—Z$ group, in which q represents 1, 2 or 3, and Y and Z, each independently represent oxygen, sulfur, $NCH_3$, NPh, $CH_2$, $C(CH_3)_2$ or $C(C_6H_5)_2$, or
- B and B' together represent an unsubstituted, monosubstituted or disubstituted 9-spirofluorene, wherein the fluorene substituents are selected from the group β, or
- B and B' together represent a saturated hydrocarbon, which is $C_3$–$C_{12}$ spiromonocyclic, $C_7$–$C_{12}$ spirobicyclic or $C_7$–$C_{12}$ spirotricyclic.

2. A compound according to claim 1, wherein at least one of the groups B and B' is a phenyl group substituted in the para position with an —$NR_6R_7$ group.

3. A compound according to claim 2, wherein the —$NR_6R_7$ group represents diphenylamino, dianisylamino, morpholinyl, thiomorpholinyl, 3,5-dimethylthio-morpholinyl, piperidinyl, azacycloheptyl, azacyclooctyl, 1,4-diaza-1-methylcyclo-heptyl, piperazinyl, pyrrolidinyl or 1,2,3,4-tetrahydroisoquinolinyl.

4. A compound according to claim 1, wherein $R_2$ in Formulas (I) and (II) is $(C_1$–$C_6)$-alkyl, phenyl, 4-methoxyphenyl, 4-dimethylaminophenyl, ethenyl, ethinyl, 2-$((C_1$–$C_6)$-alkyl)ethenyl, 2-$((C_1$–$C_6)$-alkyl)-ethinyl, 2-phenylethenyl or 2-phenylethinyl.

5. A compound according to claim 1, wherein $R_3$ in Formula (III) is $(C_1$–$C_6)$-alkyl, phenyl, 4-methoxyphenyl, 4-dimethyl-aminophenyl, ethenyl, ethinyl, 2-$((C_1$–$C_6)$-alkyl)ethenyl, 2-$((C_1$–$C_6)$-alkyl)ethinyl, 2-phenylethenyl or 2-phenylethinyl.

6. A compound according to claim 1 corresponding to Formula (I), wherein
- $R_1$, $R_3$, $R_4$ and $R_5$ each represent hydrogen;
- $R_2$ represents $(C_1$–$C_6)$-alkyl, phenyl, 4-methoxyphenyl, 4-dimethylaminophenyl, ethenyl, ethinyl, 2-$((C_1$–$C_6)$-alkyl)ethenyl, 2-$((C_1$–$C_6)$-alkyl)ethinyl, 2-phenyl-ethenyl or 2-phenylethinyl;
- B' represents phenyl, and
- B is 4-dimethylaminophenyl or 4-(N-azacycloheptyl)phenyl.

7. A compound according to claim 1 corresponding to Formula (III), wherein
- $R_1$, $R_3$, $R_4$ and $R_5$ each represent hydrogen;
- $R_2$ represents $(C_1$–$C_6)$-alkyl, phenyl, 4-methoxyphenyl, 4-dimethylaminophenyl, ethenyl, ethinyl, 2-$((C_1$–$C_6)$-alkyl)ethenyl, 2-$((C_1$–$C_6)$-alkyl)ethinyl, 2-phenyl-ethenyl or 2-phenylethinyl;
- B' represents phenyl, and
- B is 4-dimethylaminophenyl or 4-(N-azacycloheptyl)phenyl.

8. A photochromic article comprising a synthetic resin body coated or impregnated with at least one compound according to claim 1.

9. An article according to claim 8, wherein the synthetic resin body is an ophthalmic lens.

* * * * *